US012653705B2

(12) United States Patent
Ding et al.

(10) Patent No.: US 12,653,705 B2
(45) Date of Patent: Jun. 16, 2026

(54) AXIALLY COMPRESSIBLE AND STRETCHABLE BARE STENT

(71) Applicant: SHANGHAI FLOWDYNAMICS MEDICAL TECHNOLOGY CO., LTD., Shanghai (CN)

(72) Inventors: Jian Ding, Shanghai (CN); Chenying Fan, Shanghai (CN)

(73) Assignee: SHANGHAI FLOWDYNAMICS MEDICAL TECHNOLOGY CO., LTD., Shanghai (CN)

( * ) Notice: Subject to any disclaimer, the term of this patent is extended or adjusted under 35 U.S.C. 154(b) by 726 days.

(21) Appl. No.: 18/003,905

(22) PCT Filed: Nov. 6, 2020

(86) PCT No.: PCT/CN2020/127278
§ 371 (c)(1),
(2) Date: Dec. 29, 2022

(87) PCT Pub. No.: WO2022/007282
PCT Pub. Date: Jan. 13, 2022

(65) Prior Publication Data
US 2023/0255805 A1 Aug. 17, 2023

(30) Foreign Application Priority Data

Jul. 6, 2020 (CN) .......................... 202010643288.X

(51) Int. Cl.
*A61F 2/90* (2013.01)
*A61F 2/82* (2013.01)
*A61F 2/86* (2013.01)
(52) U.S. Cl.
CPC .................. *A61F 2/90* (2013.01); *A61F 2/86* (2013.01); *A61F 2/82* (2013.01);
(Continued)

(58) Field of Classification Search
CPC ...... A61F 2/04; A61F 2/07; A61F 2/82; A61F 2/86; A61F 2/88; A61F 2/885; A61F 2/90; A61F 2002/823; A61F 2210/0076
See application file for complete search history.

(56) References Cited

U.S. PATENT DOCUMENTS 6,015,432 A 1/2000 Rakos
6,592,617 B2 7/2003 Thompson
(Continued)

FOREIGN PATENT DOCUMENTS

CN 1479597 A 3/2004
CN 101234046 A 8/2008
(Continued)

OTHER PUBLICATIONS

Supplementary European Search Report in the European application No. 20944687.1, mailed on Jul. 5, 2024, 7 pages.
(Continued)

*Primary Examiner* — Dinah Baria
(74) *Attorney, Agent, or Firm* — Syncoda LLC; Feng Ma

(57) ABSTRACT

A stent for aorta is formed by weaving at least two types of filaments having different diameters, such as a first filament and a second filament. The stent is configured to be at least partially compressible and extensible along the axial direction of the stent in a natural release state, wherein the first filament has a diameter of 20-150 μm, and the second filament has a diameter of 150-800 μm. When the stent is used in the treatment of aortic aneurysm and/or aortic dissection lesions, due to the axial compressibility and extensibility of the stent, low liquid permeability and strong radial support force are provided where needed in the aorta, and due to the axial stretchability thereof, the stent can be (Continued)

easily assembled to a delivery system having an appropriate diameter. Also provided are a stent kit comprising the stent and a stent delivery system.

16 Claims, 4 Drawing Sheets

(52) U.S. Cl.
CPC . *A61F 2002/823* (2013.01); *A61F 2210/0057* (2013.01); *A61F 2210/0066* (2013.01); *A61F 2210/0076* (2013.01)

(56)                        References Cited

U.S. PATENT DOCUMENTS

| | | | |
|---|---|---|---|
| 7,052,513 B2 | 5/2006 | Thompson | |
| 7,588,597 B2 | 9/2009 | Frid | |
| 2001/0056299 A1 | 12/2001 | Thompson | |
| 2003/0100945 A1* | 5/2003 | Yodfat | A61F 2/82 |
| | | | 623/1.53 |
| 2004/0073293 A1 | 4/2004 | Thompson | |
| 2004/0215332 A1 | 10/2004 | Frid | |
| 2007/0168019 A1 | 7/2007 | Amplatz et al. | |
| 2009/0312834 A1 | 12/2009 | Wood | |

| | | | |
|---|---|---|---|
| 2017/0100231 A1* | 4/2017 | Frid | A61F 2/852 |
| 2019/0223879 A1 | 7/2019 | Jayaraman | |
| 2021/0137715 A1* | 5/2021 | Ringwala | A61F 2/966 |

FOREIGN PATENT DOCUMENTS

| | | | |
|---|---|---|---|
| CN | 101273924 A | 10/2008 | |
| CN | 102573701 A | 7/2012 | |
| CN | 203885667 U | 10/2014 | |
| CN | 203953885 U | 11/2014 | |
| CN | 105228561 A | 1/2016 | |
| CN | 205458867 U | 8/2016 | |
| CN | 209347136 U | 9/2019 | |
| CN | 110353866 A | 10/2019 | |
| CN | 212940080 U | 4/2021 | |
| EP | 1946721 A1 | 7/2008 | |
| JP | 2004520101 A | 7/2004 | |
| JP | 2012523922 A | 10/2012 | |
| JP | 2018000794 A | 1/2018 | |

OTHER PUBLICATIONS

International Search Report in the international application No. PCT/CN2020/127278, mailed on Mar. 30, 2021.
Written Opinion of the International Search Authority in the international application No. PCT/CN2020/127278, mailed on Mar. 30, 2021.

* cited by examiner

A         B         C

AXIALLY COMPRESSIBLE AND STRETCHABLE BARE STENT

CROSS-REFERENCE TO RELATED APPLICATIONS

This application is a National Stage of International Patent Application No. PCT/CN2020/127278 filed on Nov. 6, 2020, which claims priority to Chinese Patent Application No. 202010643288.X filed on Jul. 6, 2020. The disclosures of the above-referenced applications are hereby incorporated by reference in their entirety.

TECHNICAL FIELD

The disclosure relate to a bare stent, and in particular to a bare stent used in treatment of aortic lesions, such as aortic aneurysm or aortic dissection.

BACKGROUND

The arterial vessel wall is formed by tightly fitting an intima, a tunica media e and an adventitia. When an inner wall of the arterial vessel is partially damaged, the tunica media of the arterial vessel wall is gradually peeled off under a strong impact of arterial blood flow, so that blood enters between the tunica media and the adventitia of the vessel wall, thereby forming two lumens, i.e., a true lumen and a false lumen. The most common type is aortic dissection. The aortic dissection weakens the arterial wall, so that there is a risk of rupture of the aortic dissection at any time. Once the dissection ruptures, the patient will die in several minutes.

The aortic dissection is divided into two types, i.e., type A and type B (i.e., Stanford classification) according to an intima tearing site and an expansion range. Type A refers to a lesion involving an ascending aorta, which refers to a situation in which a peeling site of the arterial wall starts from the ascending aorta, and the lesion may also occur at an aortic arch or a proximal end of a descending aorta involving the ascending aorta. Type B refers to a situation in which a peeling site of the arterial wall occurs at the descending aorta without extending beyond a proximal end of an opening of a left subclavian artery.

The aortic aneurysm is also a disease in which an aorta is abnormally dilated. Rupture of the aortic aneurysm is also fatal for the patient.

Therefore, early diagnosis and timely treatment of the aortic dissection and the aortic aneurysm are essential.

At present, there are usually three solutions for treating the aortic dissection or the aortic aneurysm.

One solution is to use an open surgery through artificial vessel replacement. At present, this solution is mostly used for type A aortic dissection, and has the defects that the intraoperative mortality is high, a residual dissection is often formed after the surgery (that is, type B dissection is formed), and the re-operation rate within 10 years is up to 9%-67%. Furthermore, with this solution, the treatment cost is very high, and there are relatively few hospitals that have mastered this surgical technique. In addition, the open surgery is not suitable for all patients, thus, a very small proportion of patients may benefit from this solution.

Another solution is the EVAR endovascular intervention, i.e., a covered stent implantation. This solution has advantages of less trauma, rapid recovery and low mortality. However, the stent placement site often involves the aortic arch and/or the abdominal aorta, three branch artery vessels at the convex side of the aortic arch, as well as the major branch artery vessels at the abdominal aorta, such as the left renal artery, the right renal artery, the coeliac trunk and the superior mesenteric artery, cannot be obstructed throughout the surgery and after the surgery. Thus, the conventional practice is to perform the on-site drilling at a site of the covered stent corresponding to an important branch artery. On the one hand, difficulty of surgery is increased, so that the surgery needs to be performed by an experienced surgeon. On the other hand, once positioning of the stent is inaccurate during placement, or the stent is displaced during release, an important branch vessel may be obstructed, which may induce serious consequences. Furthermore, the stent is modified before surgery, and thus the manufacturer thereof may refuse to provide a warranty service for this reason.

A third solution is a recently proposed solution for performing total aortic endovascular intervention by using a dense mesh stent (i.e., the TEVAR intervention). Unlike the EVAR endovascular intervention, in this solution, the mechanism of mechanically obstructing the false lumen is not used, and the dense mesh stent does not significantly hinder passage of blood flow. Instead, in this solution, by creating an obstruction to blood flow at the inner wall of the lesion vessel, the hemodynamics in the false lumen is changed, the pressure in the false lumen is reduced, and the intraluminal thrombus is promoted, thereby achieving the therapeutic purposes. Due to the use of the dense mesh stent, compared with the EVAR endovascular intervention, this solution has advantages of less trauma, rapid recovery and low mortality, and the dense mesh stent does not significantly obstruct the blood flow to the branch arteries, thereby greatly reducing the difficulty of surgery. Therefore, this solution may be performed by a doctor with ordinary experience.

However, the treatment effect of this type of stent is not satisfactory. Since the tear of the inner wall of the blood vessel is not completely obstructed, an ideal intraluminal thrombus cannot be always formed. Furthermore, the existing dense mesh stents are still difficult to be applied to all lesion types of aortic dissection and aortic aneurysm, especially difficult to be applied to type A aortic lesion.

Type A aortic dissection involves the ascending aorta, and an inner diameter of the blood vessel at this site is significantly increased due to the lesion, usually up to 38-55 mm. A dense mesh stent with such a large diameter cannot be radially compressed to a stent with a very small diameter, and thus a thicker delivery system is often needed. In this case, the delivery system is difficult to be placed through a femoral artery with a relatively small diameter, even the delivery system is unable to be placed especially in Asian people with relatively thinner blood vessels. In order to reduce the diameter of the stent in a compressed state, thinner wires may be used to weave the stent. However, this results in that the radial support force of the stent is insufficient to achieve the therapeutic purposes.

SUMMARY

In view of this, a main purpose of the disclosure is to provide a stent, a stent delivery system including such a stent, and a stent placement method, which are capable of solving or improving at least one of the above problems in the related art. Specifically, a purpose of the disclosure is to provide a stent, which has a diameter suitable for delivering the stent through a femoral artery in a delivery state, and which is configured to treat the aortic dissection or the aortic aneurysm, especially type A aortic lesion. The stent may have a large diameter suitable for the aorta, especially the ascending aorta. The stent is axially stretched and radially compressed in a release state to obtain a delivery configuration with a suitable dimension, so as to perform an operation by using a delivery catheter which is delivered conventionally through the femoral artery, while obtaining the appropriate liquid impermeability and the radial support force by axial compression of the stent after it is released at a treatment site, without affecting the blood supply of the branch arteries.

To this end, a first aspect of the disclosure provides a bare stent used in an aorta. The bare stent is provided with at least two layers of woven meshes. The bare stent includes a non-sparse mesh area and an optional sparse mesh. The non-sparse mesh area is formed by overlapping and interleaving at least first wires and second wires, each of the first wires and each of the second wires having different diameters. A diameter of each of the first wires ranges from 20 μm to 150 μm, and a diameter of each of the second wires ranges from 150 μm to 600 μm. The sparse mesh area is formed only of the second wires, and the sparse mesh area is arranged at branch arteries of a corresponding treatment site after the bare stent is released. In a natural release state, except for the sparse mesh area, the bare stent has a metal coverage of at least 60%.

The stent in the disclosure is a bare stent provided with at least two layers of woven meshes and formed by overlapping and interleaving at least two kinds of wires with different diameters, i.e., the first wires and the second wires as defined above. Such an overlapping and weaving manner enables the stent to be stretchable and compressible in an axial direction thereof. According to the disclosure, the usage of the bare stent formed by weaving the first wires and the second wires with diameters in the above ranges, may obtain a relatively high radial support force when the bare stent has a braid density in a specified range, in the natural release state (i.e., without subjected to axial compression and without extension).

According to an embodiment, in the natural release state, a radial support force of the bare stent is greater than or equal to 100 N.

According to a more specific embodiment, the radial support force of the bare stent ranges from 100 N to 600 N. Except for the sparse mesh area, the bare stent has the metal coverage of 70%-90%.

The bare stent with this characteristic has a larger extensibility in the axial direction. Therefore, although the bare stent has a braid density and a radial support force much higher than those of the conventional bare stent, this bare stent may still be radially compressed to a suitable dimension more easily after it axially extends to reduce the density of woven wires per unit length, so as to be assembled into a suitable delivery system. This also allows the bare stent in the disclosure to obtain an acceptable delivery configuration dimension when it has a diameter up to 38-60 mm, so that the bare stent is even applicable to the treatment of type A dissection involving the ascending aorta. In particular, the bare stent in the disclosure may be delivered through the femoral artery by using a delivery system with a conventional outer diameter (e.g., about 5 mm to about 10 mm, preferably about 5 mm to about 7 mm), without using a delivery system with a larger outer diameter.

The stent in the embodiment has a relatively large radial support force and a relatively large braid density without compression after it is partially released, thereby facilitating immediate support and expansion of the true lumen of the blood vessel, and obstructing a tear to a certain extent. Further, the radial support force may be further enhanced and the braid density may be increased by axially compressing a local segment of the stent, so as to create the necessary radial support force and braid density, which meet the above provisions, thereby obstructing the tear on the inner wall of the blood vessel more effectively.

Therefore, when the bare stent is placed in the aorta, the bare stent has different degrees of compression in a length direction of the bare stent.

In the natural release state, the bare stent in the disclosure with a relatively high braid density may cause a certain obstruction of blood flow from the aorta to the branch artery. To this end, the bare stent is provided with a sparse mesh area over the entire area where the branch artery in the corresponding treatment site is located. The sparse mesh area is formed only of the second wires, thereby greatly reducing the braid density without hindering the blood flow at a site where the sparse mesh area is located. Unlike the covered stent windowing for each branch artery, the bare stent in the disclosure is provided with one sparse mesh area at a greater curvature, such as the aortic arch, and openings of three branch arteries at the greater curvature on the aorta are all located in the sparse mesh area, thereby reducing the difficulty of the operation. In this way, on one hand, the bare stent in the disclosure may effectively obstruct a tearing site on the vessel intima like the covered stent, and on the other hand, the bare stent in the disclosure does not require on-site windowing modification by an experienced doctor like the conventional covered stent, and does not cause any risk of obstructing the branch vessels.

According to the disclosure, when the bare stent is placed in the aorta, the bare stent has different degrees of compression in a length direction of the bare stent. Except for the sparse mesh area, the bare stent is formed by weaving the first wires and the second wires in a uniformly distributed manner.

According to an embodiment, in a release and axial maximum compression state, the metal coverage of the bare stent ranges from 90% to 100%, preferably from 90% to 95%.

According to an embodiment, in a release and axial maximum compression state, a radial support force of the bare stent is greater than or equal to 500 N, preferably from 500 N to 1000 N.

In a range of the braid density and the radial support force in the axial maximum compression state as defined above, the stent in the disclosure may effectively support a narrowed true lumen of the blood vessel even with a maximum diameter (such as 38-60 mm) suitable for the ascending aorta. In particular, a radial support force in the preferred range is particularly conducive to a lesion site which has been formed for a certain period of time, where the torn vessel intima becomes hard and thus requires a greater force to be expanded.

Therefore, in an actual application, when the stent in the disclosure is released in the blood vessel (especially the aorta), the radial support forces at different sites of the stent may vary in a range of 100-1000 N, according to compression ratios.

The aorta to which the bare stent in the disclosure is applicable especially refers to an area from the ascending aorta to an abdominal aorta, the area including at least the ascending aorta. According to one solution, the treatment site includes an aortic arch. The sparse mesh area of the bare stent in the disclosure includes a first sparse mesh area corresponding to the aortic arch site, and a central angle corresponding to the first sparse mesh area ranges from about 120° to about 180°.

In particular, the first sparse mesh area corresponds to the greater curvature of the aortic arch, especially to the branch arteries on the aortic arch: a brachiocephalic trunk, a left common carotid artery, and a left subclavian artery. Specifically, a length of the first sparse mesh area is greater than a length of the branch artery area on the aortic arch, such as 6-8 cm.

According to another solution, the treatment site further includes the abdominal aorta. The sparse mesh area of the bare stent in the disclosure further includes a second sparse mesh area corresponding to a branch artery site in the abdominal aorta. The branch arteries in the abdominal aorta are a left renal artery, a right renal artery, a coeliac trunk and a superior mesenteric artery, which are located on the abdominal aorta. A central angle corresponding to the second sparse mesh area is about 180°. Specifically, a length of the second sparse mesh area is greater than a length of a distribution area of the above-mentioned branch arteries on the abdominal aorta, such as 2-4 cm.

According to another embodiment, the bare stent is used in an area from an ascending aorta to an abdominal aorta, the area including at least the abdominal aorta. The treatment site relates to a site on the abdominal aorta with a branch vessel. The sparse mesh area of the bare stent includes a second sparse mesh area corresponding to branch artery sites in the abdominal aorta. The branch arteries in the abdominal aorta are a left renal artery, a right renal artery, a coeliac trunk and a superior mesenteric artery, which are located on the abdominal aorta. A central angle corresponding to the second sparse mesh area is 180°. Likewise, a length of the second sparse mesh area is greater than a length of a distribution area of the above-mentioned branch arteries on the abdominal aorta, such as 2-4 cm.

According to yet another embodiment, the bare stent in the disclosure is used in an area in the descending aorta without a branch vessel. The bare stent used in this area may include a non-sparse mesh area only.

In a case that the treatment site of the bare stent in the disclosure relates to the abdominal aorta site, the bare stent is internally provided with two common iliac artery stent fixing parts, which are configured to fix a left common iliac artery stent and a right common iliac artery stent. The two common iliac artery stent fixing parts are arranged inside the bare stent and correspond to the abdominal aorta close to a bifurcation of left and right common iliac arteries, and the two common iliac artery stent fixing parts are configured as two annuluses tangent to each other and are integrally formed with an inner wall of the bare stent.

Unlike a fixing part forming two cylindrical branches at a lower portion of a stent for the abdominal aorta, the two fixing parts of the bare stent in the disclosure are arranged inside the bare stent, so that the exterior of the bare stent remains to be cylindrical, which is more conducive to expanding the blood vessel, without becoming less supportive in the vicinity of the common iliac arteries. Furthermore, the common iliac artery fixing parts are integrally formed with the stent, so that the left common iliac artery stent and the right common iliac artery stent may be fixed more stably.

In different solutions, the stent may be provided with the first sparse mesh area, or may be provided with the first and second sparse mesh areas, or may be provided with the second sparse mesh area only.

Due to usage of the overlapping and weaving manner, any one of the apertures of the sparse mesh area is expandable, allowing a branch stent to be placed through the expanded aperture.

The bare stent according to this embodiment may be woven according to the braid density requirements for portions of the stent other than the sparse mesh area. After weaving is completed, the first wires are removed in an area where the sparse mesh area is intended to be formed, thereby forming the sparse mesh area.

According to the disclosure, the bare stent may have a variable diameter, and the diameter of the bare stent ranges from 20 mm to 60 mm, preferably from 20 mm to 55 mm.

According to another embodiment, a diameter of a portion of the bare stent ranges from 38 cm to 60 cm, preferably from 38 mm to 55 mm. In the release state, the bare stent in this embodiment may be provided with a first segment at a proximal end portion of the bare stent. The first segment may have a diameter of 38-60 cm, preferably 38-55 mm, so as to be suitable for the ascending aorta. A length of the first segment ranges from 8 cm to 11 cm, preferably from 8 cm to 10 cm. The bare stent may be further provided with a second segment adjacent to the first segment. The second segment may have a diameter of, for example, 20-35 mm, so as to be suitable for the aortic arch, even suitable for a portion extending to the abdominal aorta. The second segment extends from the first segment to a distal end of the bare stent. A length of the second segment may range from 20 cm to 35 cm, preferably from 25 cm to 30 cm. The above two segments may also be formed into two stents, respectively. The second segment stent partially extends into the interior of the first segment stent during placement. The second method is more flexible. If necessary, a stent with three separate segments may also be formed to facilitate operation.

The bare stent in the disclosure is particularly advantageous for type A aortic dissection involving the ascending aorta. It is well known that the ascending aorta has a large inner diameter, but has a relatively short straight part, and the distal end of the ascending aorta is an aortic arch turning nearly 180°. This results in a more difficult release of the stent in the ascending aorta. The bare stent in the disclosure has a certain braid density and radial support force in the natural release state. Thus, only a small axial compression is required to obtain the expected effective obstruction of a tearing site in the aortic intima. As can be seen from a stent release method described in detail below in combination with the specific embodiments, an expected effect may be obtained after a relatively short segment of the stent is released in the ascending aorta to be compressed with a relatively low proportion. Therefore, the bare stent in the disclosure is particularly advantageous for the treatment of the ascending aorta site with a relatively short straight part.

According to other embodiments, the bare stent may be only provided with a portion corresponding to an area from the descending aorta to an auxiliary aorta, and thus has a diameter of 20-35 mm and a length of 20-30 cm, for example.

According to an embodiment, the bare stent is formed by weaving three kinds of wires with different diameters. The second wires may include first thick wires and second thick wires, each of the first thick wires and each of the second thick wires having different diameters. According to a specific embodiment, a diameter of each of the first thick wires may range from 150 μm to 300 μm, and a diameter of each of the second thick wires may range from 300 μm to 600 μm.

According to another embodiment, the bare stent is formed by weaving three kinds of wires with different diameters. The first wires may include first thin wires and second thin wires, each of the first thin wires and each of the second thin wires having different diameters. According to a specific embodiment, a diameter of each of the first thin wires may range from 50 μm to 100 μm, and a diameter of each of the second thin wires may range from 100 μm to 150 μm.

According to yet another embodiment, the bare stent may be formed by weaving four kinds of wires with different diameters, i.e., the first and second thin wires as well as the first and second thick wires as described above.

The number of wires for weaving the bare stent may be 96-202, preferably 96-156. The number of second wires may be 4 or more, such as 4-30 or 4-24, and the remaining wires are the first wires.

According to an embodiment, when the thick wires with two different diameters are used, the second wires include 6-12 first thick wires and 4-12 second thick wires, and the remaining wires are the first wires.

If the number of thick wires (i.e., second wires) is excessive, the stent cannot be effectively compressed to the desired delivery state. However, if the number of thick wires is too small, the stent cannot provide the expected radial support force even after being compressed, and the expected structure and morphology of the stent cannot be maintained in the release state.

According to another embodiment, when the thin wires (the first wires) with two different diameters are used, 4-30 wires, preferably 4-24 wires are the second wires, and the remaining wires are the first wires. The first wires include 32-166 first thin wires and 32-66 second thin wires, provided that a sum of a number of the first thin wires and a number of the second thin wires is less than or equal to 198.

The braid density and the radial support force of the bare stent in the disclosure may be obtained, and the radial compression ratio may be taken into account by increasing the number of layers of woven meshes.

According to an embodiment, the bare stent is formed of at least two layers of woven meshes. According to an embodiment, the stent is provided with two to four layers of woven meshes, preferably four layers of woven meshes.

A method for weaving the stent in the disclosure is not specifically limited. A conventional overlapping and weaving method may be used (that is, there is no constraint at an intersection between the wires), as long as it may facilitate the axial compression and stretching of the stent.

It should be understood that according to a radial support force range and a braid density range required by a specific treatment type, those skilled in the art may select a suitable woven material and determine a reasonable number of layers under specific equipment conditions according to the descriptions herein, further select a suitable diameter, number, or the like of the wires, and determine a suitable weaving solution to obtain a stent having the desired radial support force range and metal coverage range. For example, the suitable weaving solution may be designed by dedicated software.

According to a further embodiment, a tip of the bare stent in the disclosure (especially the proximal end, at which the stent has a maximum radial support force) may be formed in a return weaving manner. As for the other tip of the bare stent, if there is a burr which cannot be woven in a return weaving manner again, the burr may be positioned on an inner side of the bare stent by selecting a suitable arrangement of each layer. Alternatively, if there are two layers of burrs, one of the two layers of burrs is woven in a return weaving manner by a small distance, so as to wrap the other one of the two layers of burrs in the segment which is woven in a return weaving manner. Alternatively, if multiple stents are used in conjunction with each other, a single layer of burr or two layers of burrs may be overlapped in another dense mesh stent. The bare stent in this embodiment is provided with a smooth tip, thereby avoiding mechanical damage to the inner wall of the blood vessel by the exposed wire tip (burr).

The bare stent in the disclosure is self-expandable or capsule-expandable. Materials of the first wires and the second wires for weaving the bare stent may be different, but preferably the same. Generally, the material of the wire may be metal, such as a shape memory alloy (e.g., Nitinol), cobalt-chromium alloy, tungsten, or tantalum.

DETAILED DESCRIPTION

Figure 1:
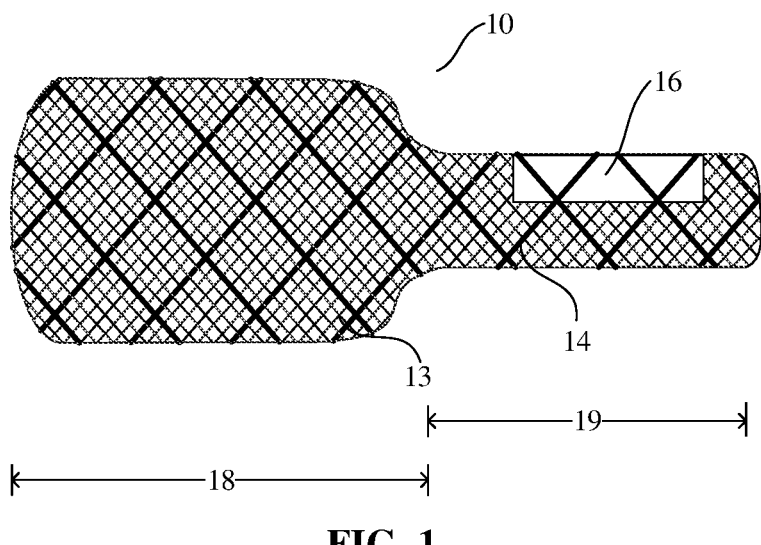
FIG. 1 is a schematic view of a single layer of a bare stent according to an embodiment of the disclosure.

Technical solutions in embodiments of the disclosure will be clearly and completely described below in combination with the embodiments of the disclosure and the accompanying drawings. It is apparent that the described embodiments are only part of the embodiments of the disclosure, rather than all the embodiments, and the technical solutions recited in the embodiments of the disclosure may be implemented in any combination without conflict. All other embodiments obtained by those of ordinary skill in the art based on the embodiments of the disclosure without any creative efforts belong to the protection scope of the disclosure.

Throughout the description, terms used herein should be understood as meanings as usually used in the art, unless specifically stated otherwise. Therefore, unless defined otherwise, all technical and scientific terms used herein have same meanings as usually understood by those skilled in the art to which the disclosure belongs. When there is a contradiction, meanings of the description are preferred.

Like reference numerals in the accompanying drawings refer to like components. Shapes and dimensions of components in schematic drawings are for illustration only and cannot be considered to reflect actual shapes, dimensions and absolute positions.

It should be noted that in the disclosure, terms "including", "include", or any other variants thereof are intended to cover a non-exclusive inclusion, so that a method or device including a series of elements not only includes elements which are explicitly recited, but also includes other elements which are not explicitly listed, or further includes elements inherent to implementation of the method or device.

It should be noted that terms "first\second" involved in the embodiments of the disclosure are only intended to distinguish similar objects, and do not represent a specific sequence of the objects, and it may be understood that "first\second" may exchange a specific sequence or order in an allowable situation. It should be understood that objects distinguished by "first\second" may be interchanged in an appropriate situation, to enable embodiments of the disclosure described here to be implemented in an order other than those illustrated or described herein.

In order to describe the disclosure more clearly, terms "proximal end" and "distal end" are customary terms used in the field of intervention medical treatment. Herein, "distal end" indicates an end away from the heart during operation, and "proximal end" indicates an end close to the heart during operation.

Herein, unless stated otherwise, terms "bare stent" and "stent" may be used interchangeably and have the same meaning, that is, these terms refer to a bare stent. The disclosure provides a bare stent used in an aorta. The bare stent is provided with at least two layers of woven meshes, and is formed by overlapping and interleaving at least first wires and second wires, each of the first wires and each of the second wires having different diameters. A diameter of each of the first wires ranges from 20 μm to 150 μm, and a diameter of each of the second wires ranges from 150 μm to 600 μm. In a natural release state of the bare stent, except for a sparse mesh area, the bare stent has a metal coverage of at least 60%. The bare stent may further be provided with at least one sparse mesh area. The sparse mesh area is formed only of the second wires, and the sparse mesh area is arranged at branch arteries of a corresponding treatment site after the bare stent is released.

FIG. 1 shows a schematic view of a single layer of a bare stent 10 according to an embodiment of the disclosure. As shown in FIG. 1, the bare stent 10 is provided with a segment 18 suitable for the ascending aorta and a segment 19 suitable for the aortic arch. A diameter of the segment 18 suitable for the ascending aorta ranges from about 38 mm to about 60 mm, and a diameter of the segment 19 suitable for the aortic arch is reduced to about 25 mm to about 35 mm. The bare stent 10 may be provided with multiple layers, such as 4 layers, so as to obtain the desired braid density. In order to clearly illustrate a specific structure of the bare stent, only a single layer is shown in FIG. 1. Each layer of the bare stent 10 is formed by interleaving the first wires (thin wires) 13 and the second wires (thick wires) 14. A sparse mesh area 16 is provided in the segment 19 suitable for the aortic arch. The sparse mesh area 16 is only provided with the second wires (i.e., the thick wires) 14. The sparse mesh area 16 is arranged at a site corresponding to a greater curvature of the aortic arch after the stent is released, and the sparse mesh area is provided with an area larger than an opening of the branch vessel of the greater curvature in the artery. Typically, the sparse mesh area 16 may have a length of about 6-8 cm, and a width occupying about ⅓-½ arc length of the circumference of the segment 19 of the stent 10, or a corresponding central angle of about 120° to about 180°.

Since the bare stent is formed by weaving wires with at least two different kinds of diameters, the stent body is configured to be at least partially compressible and extendable along an axial direction of the stent in the release state.

The bare stent 10 in the disclosure is formed by weaving in an overlapping manner, and any relative movement may happen at an intersection between the wires, so that any aperture on the stent 10 in the disclosure may be easily expanded or compressed. The bare stent thus formed may be axially compressed or stretched along a central axis thereof, when fixed at an end thereof.

Figure 2:
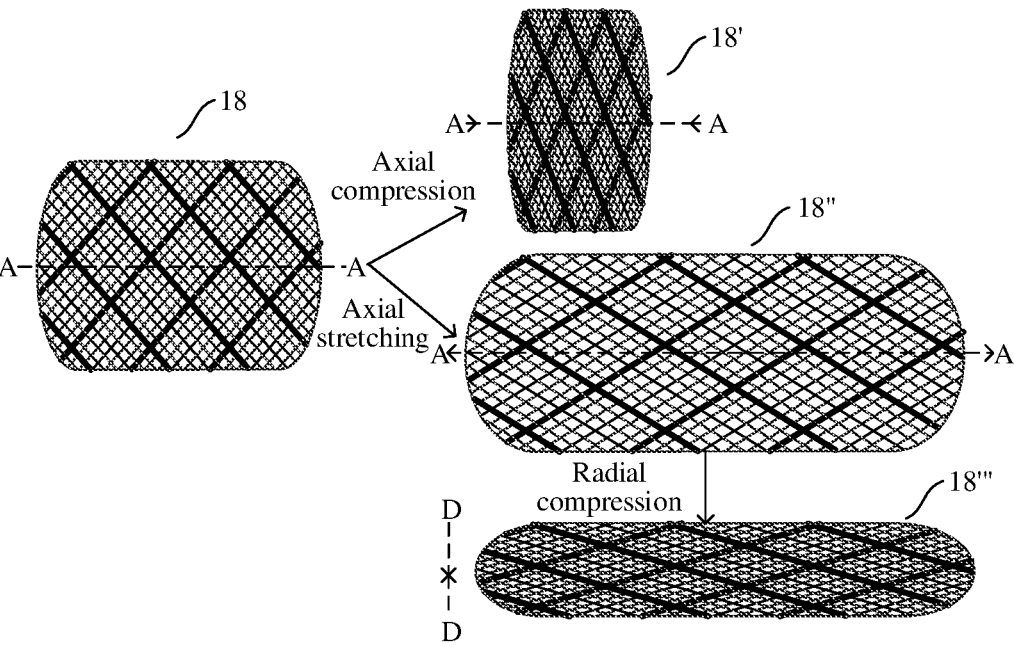
FIG. 2 is a schematic view of axial compression and axial stretching as well as radial compression after the axial stretching of a local segment of the bare stent shown in FIG. 1.

With reference to FIG. 2, a situation where a local segment 18 of the bare stent 10 shown in FIG. 1 is axially compressed 18' and axially stretched 18", and the axially stretched segment 18" is further radially compressed 18''' is schematically shown.

The "axial direction" of the stent as mentioned herein refers to a direction along A-A as shown in FIG. 1, which is a direction of a central axis of a cylindrical shape of the stent. The "radial direction" of the stent as mentioned herein refers to a direction along D-D as shown in FIG. 1, which is a diameter direction of a circle of the cylindrical shape of the stent. In general, "axially compressed/stretched" herein refers to compression/stretching in a direction along the A-A axis, and "radially compressed" refers to compression in a direction from the circumference to the center of the circle.

As shown in FIG. 2, the above characteristics of the bare stent in the disclosure may provide many benefits. According to a stent placement method described in detail below, the bare stent in the disclosure may be partially released during placement (for example, the segment 18 at the ascending aorta is released) and axially compressed, the compressed segment 18' of the stent forms a high braid density, and the density of the second wires per unit length is increased to obtain a high radial support force. The high radial support force may achieve effective expansion of a narrowed part of the blood vessel, and the high braid density may achieve very low fluid permeability, thereby effectively obstructing the tear of the vessel intima. In this case, the second wires 4 in the segment 18' at the ascending aorta act as a support skeleton, and the first wires fill the gaps between the second wires to act as a fabric membrane similar to a covered stent. Unlike the covered stent, the bare stent in the disclosure may provide a relatively high radial support force after being axially compressed, which is difficult to achieve by the covered stent, and thus the bare stent in the disclosure may even be effectively used for the treatment of type A aortic dissection involving the ascending aorta. Furthermore, since the stent may be axially stretched, the density of the wires, especially the second wires, for weaving the stent after being properly stretched (see segment 18" shown in FIG. 2) is significantly reduced per unit length. Thus, in this case, the stent is easily compressed to a smaller diameter by radial compression (see segment 18''' shown in FIG. 2), so as to be assembled into a delivery system with a conventional outer diameter (e.g., 5-10 cm, preferably 5-7 cm). Therefore, the bare stent in the disclosure solves the following problems in the related art: a stent with a large dimension and a high support force cannot be assembled into a delivery system with a suitable diameter, and a conventional dense mesh stent or covered stent is difficult to be applied into the ascending aorta.

In a natural release state, a radial support force of the bare stent in the disclosure may be no less than 100 N. In an axial maximum compression state, a radial support force of the bare stent in the disclosure may be no less than 500 N.

The "natural release state" of the stent as mentioned herein refers to a state in which the stent is not axially compressed and released, when it is fixed in a water bath at 37±2° C.

The "axial maximum compression state" of the stent as mentioned herein refers to a state in which the stent is axially compressed until it is unable to be further compressed, when it is in the natural release state.

The "radial support force" of the stent as mentioned herein refers to a force required to compress the stent along a diameter direction to reach 85% of its original diameter, after it is fixed in the natural release state.

Along with the radial support force, the stent in the disclosure also requires a high liquid impermeability to obtain an effect of effectively obstructing the tear of the vessel intima. This property may be represented by the braid density. In the natural release state, the metal coverage of the stent 1 in the disclosure may be more than 60%, and up to 90%. In the axial maximum compression state, the metal coverage of the stent 1 in the disclosure may range from 90% to 100%, preferably from 90% to 95%.

The "metal coverage" of the stent as mentioned herein refers to a metal coverage ratio per unit area measured by electron microscope scanning. A sum of the metal coverage and a void ratio per unit area should be 100%.

Although FIG. 1 only shows a single layer, the stent in the disclosure has a structure with multiple layers, such as 2-4 layers. For example, the multiple layers may be formed in a return weaving manner.

According to the disclosure, the stent 1 may be formed by weaving a total of 96-202 wires. For example, as may be enumerated, the stent in the disclosure may be formed by weaving 96, 128, 160, 196 wires. The number of wires may be determined according to the diameter of the stent, the number of layers, the materials of the used wires, or the like.

The material of the stent in the disclosure may be any material suitable for a peripheral vascular stent, as long as the material may provide a sufficient radial support force and have certain fineness. Generally, metal wires such as nickel-titanium alloy wires, cobalt-chromium alloy wires, tungsten wires, tantalum wires, or the like are preferably used, more preferably the nickel-titanium alloy wires.

There are at least four second wires 4 used as thick wires. Generally, the number of the second wires is no more than 30, which, for example, may be 8, 10, 12, 14, 16, 20, 24, 28. The diameter of the second wire 4 is comprised between 150 μm and 800 μm, preferably between 150 μm and 600 μm, such as 150 μm, 200 μm, 250 μm, 300 μm, 350 μm, 400 μm, 450 μm, 500 μm, 550 μm, or 600 μm. The second wire 4 provides a basic support force and a complete structure for the stent 1. However, the number of second wires cannot be too much. For example, even though only wires with the diameter of 300 m are used, when there are about 32 wires, it is difficult to compress the stent, especially for a stent portion with ultra-large diameter greater than about 40 mm, to a suitable delivery dimension, so that the stent cannot be used.

In the stent 1, except for the thick wires, the remaining wires are the first wires 3 used as thin wires. The first wire 3 of the disclosure may have a diameter of 20-150 μm, preferably a diameter of 50-150 μm, such as 50 μm, 60 μm, 70 μm, 80 μm, 90 μm, 100 m, 110 μm, 1120 μm, 130 μm, 140 μm and 150 am. The first wires 3 provide the functions of auxiliary supporting the stent 1 and filling gaps between the second wires 4. Furthermore, since the number of the first wires 3 is much greater than that of the second wires 4, the first wires 3 also provides a function of maintaining the shape of the stent 1. The inventors have found that although it seems to be feasible theoretically, in fact, with the overlapping and weaving method in the disclosure, a large-diameter stent with a certain shape and a sufficient support force cannot be formed by the second wires (i.e., the thick wires) alone. Furthermore, a large-diameter stent with a fixed wire-to-wire intersection formed by using for example a laser engraving technology, has a much smaller support force, even though the diameter of the wires is the same, which cannot meet the requirements for use in the aortic vessel in the disclosure.

According to another example, the bare stent in the disclosure may be suitable for the entire arterial area from the ascending aorta to the abdominal aorta.

Figure 3:
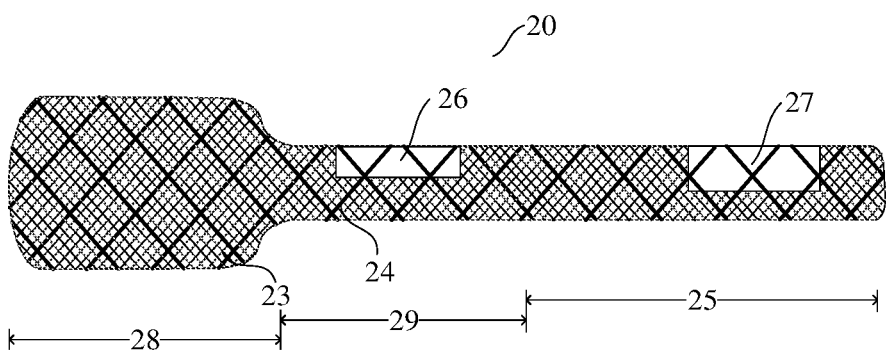
FIG. 3 is a schematic view of a bare stent according to another embodiment of the disclosure.

With reference to FIG. 3, a schematic view of a single layer of a bare stent 20 provided with two sparse mesh areas according to another embodiment of the disclosure is schematically shown. Although FIG. 3 only shows a single layer, the bare stent 20 in this embodiment may be provided with 2-4 woven layers which are woven in the same manner.

As shown in FIG. 3, the bare stent 20 includes a segment 28 corresponding to the ascending aorta, a segment 29 corresponding to the aortic arch, and a segment 25 corresponding to an area from the descending aorta to the abdominal aorta. The segment 28 corresponding to the ascending aorta may have a diameter of 38-60 mm, such as 38-55 mm, and a length of 8-11 cm. The segment 29 corresponding to the aortic arch may have a diameter gradually reduced in a range of 20-45 mm, such as about 20-35 mm. The segment 25 corresponding to the area from the descending aorta to the abdominal aorta may extend from an area behind the aortic arch to an area of the abdominal aorta, and a diameter of the segment 25 may vary from about 25 mm-about 30 mm to about 20 mm-about 25 mm. The segment 29 corresponding to the aortic arch may have a length of 8-11 cm, and the segment 25 corresponding to the area from the descending aorta to the abdominal aorta may have a length of 20-35 cm for example.

The bare stent 20 in this embodiment is also formed by interleaving the first wires 23 and the second wires 24.

According to a variant embodiment, the above three segments may be made into three independent stents respectively, which may be flexibly combined for usage. During usage, the proximal end of the stent farther away from the heart is inserted into the distal end of the stent closer to the heart, thereby fixing the relative position of each stent.

The bare stent 20 may include two sparse mesh areas formed only of the second wires 24, i.e., a first sparse mesh area 26 corresponding to the branch arteries (a brachio-cephalic trunk, a left common carotid artery, and a left subclavian artery) at the aortic arch, and a second sparse mesh area 27 corresponding to the branch arteries (a left renal artery, a right renal artery, a coeliac trunk, and a superior mesenteric artery) at the abdominal aorta. The first sparse mesh area may have a dimension in the embodiment as shown in FIG. 1. The second sparse mesh area may have a length of about 2-4 cm, and a width occupying about ½ arc length of the circumference of this segment.

The bare stent shown in FIG. 1 and FIG. 3 may be formed by weaving in a conventional manner, and then the first wires 13, 23 in predetermined areas are removed to form the sparse mesh areas 16, 26, 27.

Figure 4:
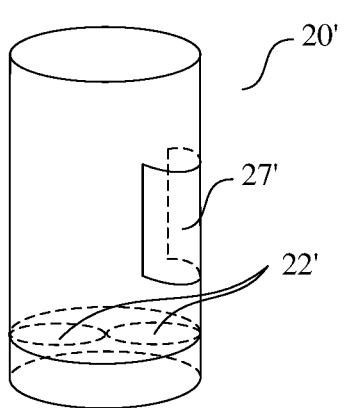
FIG. 4 is a schematic view of a bare stent according to yet another embodiment of the disclosure.

According to a further embodiment, at a corresponding treatment site which is the abdominal aorta, the bare stent in the disclosure may be provided with two common iliac artery stent fixing parts, which are configured to receive and fix a left common iliac artery stent and a right common iliac artery stent. With reference to FIG. 4, a bare stent in this embodiment is schematically shown. The stent 20' shown in FIG. 4 is suitable for a segment of the abdominal aorta and is provided with a sparse mesh area 27'. The two common iliac artery stent fixing parts 22' configured as two adjacent annular channels are provided inside the stent 20' at the lower portion of the stent 20'. For the sake of clarity, the fixing part 22' is shown as a plane in FIG. 4. In fact, the fixing part 22' has a certain thickness. In some examples, the common iliac artery stent fixing part 22' may extend downward to a lower end of the stent 20'.

The common iliac artery stent fixing part 22' is also formed by weaving the same first and second wires as the stent 20' (the first and second wires are not shown), and is integrally formed with the bare stent. The exteriors of the two annuluses are integrally woven with an inner wall of the stent 20'. The inner diameters of the two annuluses are adapted to the outer diameters of the left and right common iliac artery stents to be received and fixed, usually slightly smaller than the outer diameters of the left and right common iliac artery stents, so as to fix the common iliac artery stents.

Figure 5:
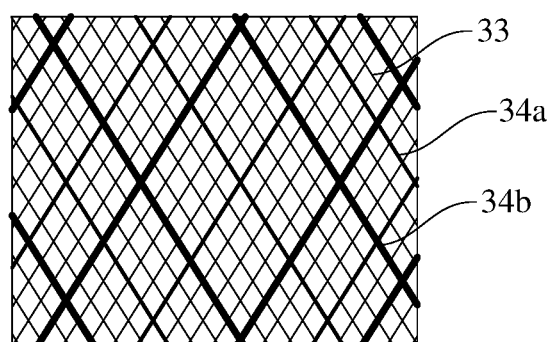
FIG. 5 is a schematic partially enlarged view of a bare stent according to an embodiment of the disclosure.

According to an embodiment, the stent in the disclosure may also be formed by weaving three wires with different diameters. As shown in FIG. 5, a schematic partially enlarged view of a single layer of the stent in this embodiment is shown. The stent is formed by weaving one kind of first wire 33 and two kinds of second wires 34a, 34b. The first wires 33 are thin wires, which may have a diameter of 50-150 μm. The second wires include first thick wires 34a which may have a diameter of 150-300 μm, and second thick wires 34b which may have a diameter of 300-600 μm. 6-12 first thick wires may be used, more than 4 but no more than 12 second thick wires may be used, and the remaining wires are the first wires. This embodiment may also have other variations, for example, the stent is formed of two kinds of first wires (for example, their diameters are in a range of 20-100 μm and a range of 100-150 μm, respectively) and one kind of second wire, or formed of two kinds of first wires and two kinds of second wires, which is not limited thereto.

A radial support force of the stent formed of three or more kinds of wires with different diameters is more uniform throughout the stent, and the flexibility of the stent may also be enhanced.

Figure 6:
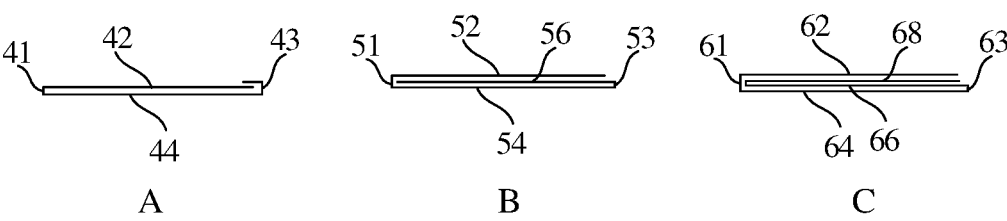
FIG. 6 is a schematic cross-sectional view of a multi-layer stent wall of a bare stent according to the disclosure.

As described above, the bare stent in the disclosure may be provided with multiple layers, preferably two layers, three layers, or four layers. According to a preferred embodiment, the multi-layer bare stent may be formed by return weaving a single-layer woven mesh. As shown in A to C in FIG. 6, schematic cross-sectional views of walls of stents with two to four layers are shown. A in FIG. 6 shows a two-layer structure. An upper layer 42 of the structure in this figure is located at a side of the stent close to interior, and a lower layer 44 is located at a side of the stent close to exterior (i.e., a side in contact with the vessel wall). In this structure, a smooth tip is formed at a proximal end 41 in a return weaving manner. At a distal end 43, the lower layer 44 facing toward the exterior of the stent is woven in a return weaving manner by a certain distance, so as to wrap an opened edge (burr) at a distal end of the upper layer 42 facing toward the interior of the stent, inside the lower layer 44, thereby forming two smooth tips at both ends. Similarly, in B in FIG. 6, an upper layer 52 is woven in a return weaving manner at a proximal end 51 to form a lower layer 54, and the upper layer 52 is further woven in a return weaving manner at a distal end 53 to form an intermediate layer 56. At the distal end 53, the lower layer 54 and the intermediate layer 56 are slightly longer than the upper layer 52, so that an opened edge at the distal end of the upper layer is located inside the bare stent. In this way, both ends of the bare stent are also smooth tips. The same principle is also applied to four layers in C in FIG. 6. At a distal end 63, two layers 62, 68 close to the interior of the bare stent are shorter than an edge formed by return weaving two layers 64, 66 close to the exterior of the bare stent, while at a proximal end 61, a lowermost layer 64 is formed by return weaving an uppermost layer 62, so as to wrap two intermediate layers 68 and 66 therebetween. One variation may be realized by return weaving a small segment at the distal end of one of the uppermost layer 62 or the intermediate layer 68 again, so as to wrap an opened edge of the other one of the uppermost layer 62 or the intermediate layer 68 therebetween. In this way, both ends of the bare stent are completely smooth tips.

The stent in the disclosure is described in detail as above by way of examples. It should be understood by those skilled in the art that the above examples are intended to explain advantages of the stent in the disclosure, rather than limiting the scope of the disclosure, and features in an example may be applied to the stent in other examples separately or in combination in an appropriate situation. Apparent variations and modifications made to the stent by those skilled in the art according to contents of the disclosure herein, fall within the scope of the disclosure, as long as they meet the concept of the disclosure.

A stent delivery system for placing the bare stent in the disclosure and a method for placing the bare stent are exemplarily described below.

Although the bare stent in the disclosure has a diameter of up to 38-60 mm and a braid density of 60%-90%, as described above, the bare stent may still be compressed to a delivery configuration with a suitable diameter, so as to be assembled in a delivery system with a conventional outer diameter. In the delivery system, the above-mentioned stent in the disclosure is assembled in the system in a delivery configuration, and both ends of the stent are removably constrained, and the constraints are removed only after other portions of the stent are released, thereby allowing the stent to be completely released.

Figure 7:
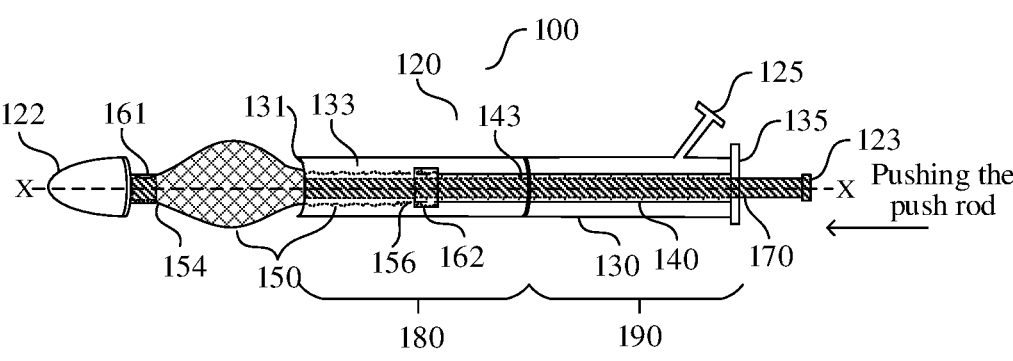
FIG. 7 is a schematic view of a stent delivery system for a bare stent according to the disclosure.

With reference to FIG. 7, a schematic view of a stent delivery system 100 in a semi-release state according to the disclosure is shown. The stent delivery system 100 includes a delivery catheter 120 and a stent 150.

The delivery catheter 120 includes an outer catheter 130, an inner catheter 140 and a push rod 170, which are arranged coaxially each other and sequentially arranged from exterior to interior along a longitudinal axis X-X. The delivery catheter 120 is provided with a distal end 123 and a proximal end 122. The delivery catheter 120 is further provided with a hemostatic valve 125. The outer catheter 130 is provided with a proximal end portion 180 and a distal end portion 190, and a first hollow cavity 133 penetrates through the entire outer catheter 130. The inner catheter 140 is arranged coaxially with the outer catheter 130 along the longitudinal axis X-X and arranged in the first hollow cavity 133 at the distal end portion 190 of the outer catheter, and the inner catheter 140 is provided with a second hollow cavity 143. The push rod 170 extends in the first hollow cavity of the outer catheter 130 from the proximal end 123 and extends through the second hollow cavity 143 of the inner catheter 140, until extending beyond a port 135 of the distal end of the outer catheter. The push rod 170 may be provided with a third hollow cavity (not shown) for passage of a guide wire.

At the proximal end portion 180 of the outer catheter 130, the stent 150 is releasably maintained in the first hollow cavity 133 arranged between the push rod 170 and the outer catheter 130 in a delivery configuration. A first constraint component 161 constrains a proximal end 154 of the stent 150 at a proximal end of the push rod 170. The first constraint component 161 may be a conventional stopper which may be removed from the stent 150 if necessary, thereby allowing the proximal end 154 of the stent 150 to be released. A second constraint component 162 constrains a distal end 156 of the stent 150 at a proximal end of the inner catheter 140. Similarly, the second constraint component 162 may be a conventional stopper which may be removed from the stent 150 if necessary, thereby allowing the distal end 156 of the stent 150 to be released.

According to the delivery system 100 in this embodiment, a proximal end 131 of the outer catheter 130 may be separated from the proximal end 122 of the delivery catheter 120, and the outer catheter 130, the inner catheter 140 and the push rod 170 may be moved relative to each other by pushing the push rod 170 toward the proximal end or by pulling the outer catheter 130 toward the distal end.

In the system 100 shown in FIG. 7, by pushing the push rod 170 toward the proximal end 122, the proximal end 122 of the delivery catheter 120 drives the push rod 170 fixedly connected thereto and the stent 150 constrained together with an end of the push rod 170 to move toward the proximal end relative to the outer catheter 130. In this way, the stent 150 starts to be released from the proximal end 154 thereof.

The stent delivery system in the disclosure is particularly advantageous for the treatment of type A aortic dissection.

Figure 8:
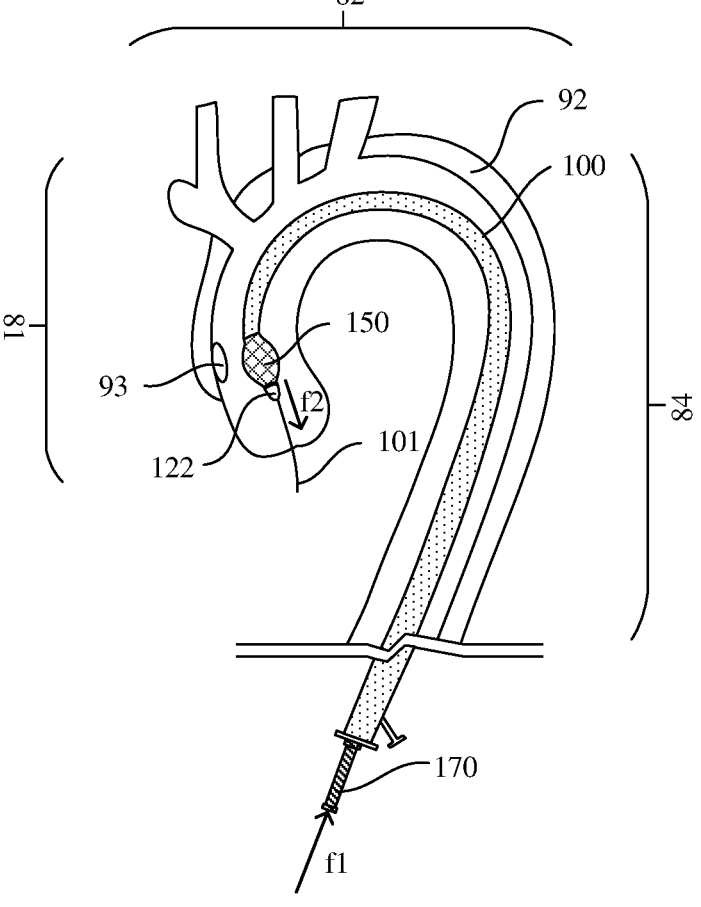
FIG. 8 is a schematic view of placing a bare stent according to the disclosure in type A aortic dissection lesion by using a stent delivery system.

With reference to FIG. 8, a schematic view of placing a stent 150 in type A aortic dissection lesion by using a stent delivery system 100 in the disclosure is shown, in order to explain the therapeutic advantages of the stent delivery system in the disclosure on type A aortic dissection. FIG. 8 shows that there is a tear 93 in an ascending aorta 81. Thus, a false lumen 92 is formed from the ascending aorta 81, through an aortic arch 83 to a descending aorta 84. The stent delivery system 100 in the disclosure has been guided into a true lumen 91 of the aorta by a guide wire 101. When the stent 150 starts to be released, the operator pushes the push rod 170 in a direction toward the proximal end, where the pushing force is indicated by f1, and the direction of the pushing force is indicated by an arrow directed upward along the descending aorta. The pushing force f1 is transmitted to the proximal end 122 of the delivery catheter along the push rod 170. In this case, since the delivery system 100 turns nearly 180° after passing through the aortic arch 83, a force f2 acting on the proximal end 122 of the delivery catheter has a direction nearly opposite to a direction of the pushing force f1 (as indicated by the arrow). This causes difficulty in controlling a magnitude of the pushing force required during initial release of the stent. In the stent delivery system 100 in the disclosure, with reference to FIG. 8, the proximal end of the stent 150 is temporarily constrained at the proximal end of the push rod 170 by a member, such as a stopper, thereby significantly reducing an outward expansion force of the stent 150 at the proximal end, and reducing the friction between the stent 150 and an inner wall of the outer catheter 130. Therefore, the pushing force required when the stent is initially released by the delivery system 100 in the disclosure is significantly reduced, and the proximal end of the push rod 170 may be easily pushed out of the outer catheter 130.

Figure 9:
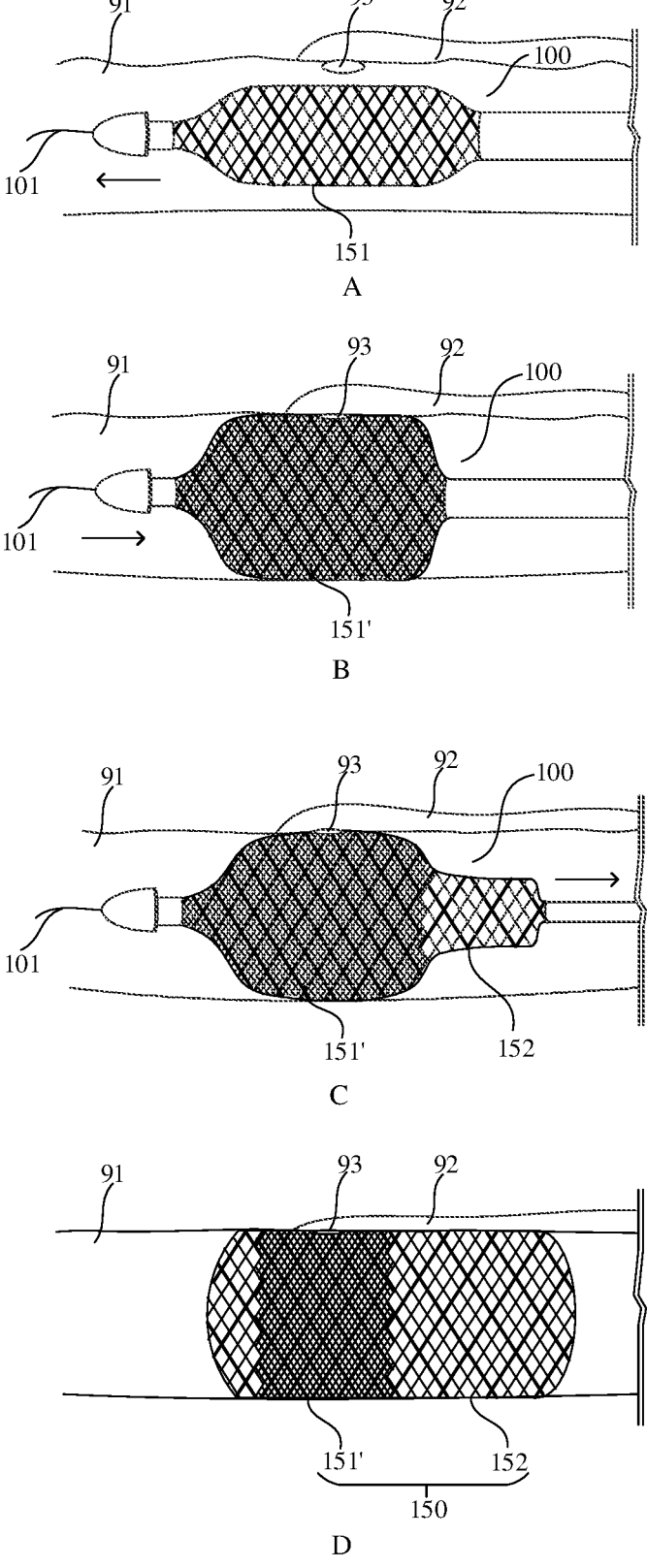
FIG. 9 is a schematic view of placing a bare stent according to the disclosure at a tear of an aortic intima by using a stent delivery system.

With reference to FIG. 9, a schematic view of placing a stent at a tear of an aortic intima by using the stent delivery system in the disclosure is shown. A segment of aortic vessel 91 including a tear 93 of the vessel intima is shown in A in FIG. 9. Tearing of the intima is induced by the tear 93 to form a false lumen 92. The stent delivery system 100 in the disclosure has been guided to the tear 93, and has released a segment 151 of the stent by pushing the push rod in a direction indicated by the arrow in a case that a position of the outer catheter 130 remains unchanged. With reference to B in FIG. 9, positions of the inner and outer catheters of the delivery system 100 remain unchanged, and the push rod is pulled back in a direction of the arrow in this figure, so that the released segment 151 of the stent is compressed back and finally abuts against a blood vessel area where the tear 93 of the vessel intima is located, thereby forming a compressed segment 151'. When the stent is designed, the diameter of the stent is usually designed to be slightly greater than the diameter of the blood vessel at the placement site, so that the compressed segment 151' abuts tightly against an inner wall of this segment of the blood vessel, obstructs the tear 93, and expands a true lumen of this segment of the blood vessel. The compressed segment 151' remains in this segment of the blood vessel in the compressed shape, since the compressed segment is subjected to an inward contraction force of the vessel wall.

Next, as shown in C in FIG. 9, the remaining segment 152 of the stent is further released by pulling the outer catheter 130 toward the distal end in a direction indicated by the arrow in this figure (the inner catheter 140 and the push rod 170 remain stationary). Finally, after the stent 150 is completely released, constraints of stoppers on both ends of the stent are removed, so that the entire stent 150 is released to the treatment site. Then the delivery catheter is withdrawn from the blood vessel (see D in FIG. 9). The stent 150 placed at the lesion site is provided with two segments, one is the compressed segment 151', and the other is a natural release segment 152. The compressed segment 151' provides functions of obstructing the tear 93 and providing a relatively strong radial support to the blood vessel. The natural release segment 152 provides a function of supporting other parts of the blood vessel properly, and does not hinder the blood flow, and in particular does not hinder the blood flow toward the branch vessel.

According to the disclosure, after the segment 151 of the stent is released (i.e., a state shown in A in FIG. 9), the position of the stent may be confirmed, so that the tear 93 may be accurately obstructed by the compressed segment. If the position is not ideal enough, adjustment may be performed, or even the released segment 151 is withdrawn into the outer catheter again, and is re-released after the position of the delivery system is adjusted.

Likewise, the position of the stent may be confirmed after any segment is released, so as to achieve a best placement effect. Finally, the position of the stent is reconfirmed before the constraints on both ends of the stent are removed, since the stent may be withdrawn and rereleased when its placement position is found to be not ideal at this time. After the constraints on both ends of the stent are removed, the position of the stent cannot be adjusted.

Furthermore, other segments of the stent are compressed in a similar manner to that shown in B in FIG. 9. For example, when a front portion of the stent is released and has abutted against the vessel wall, a segment of the stent continues to be released. Since an end of the subsequently released stent is constrained by the outer catheter, the push rod may remain stationary, and the outer catheter and the inner catheter may be moved simultaneously toward the proximal end, so that a new segment of the stent is released. However, a segment of the stent, which does not abut against the vessel wall yet, is compressed and abuts against the vessel wall, so as to form a segment with a high metal coverage and a high radial support force.

Detailed solutions of the stent delivery system in the disclosure and the method for placing the stent into the blood vessel by using such a system are explained by the above examples. Variations and modifications may be readily made by those skilled in the art based on the above contents, to be adapted to actual application requirements without departing from the spirit of the disclosure, these variations and modifications also fall within the scope of the disclosure.

Embodiment

This embodiment provides a bare stent provided with a structure shown in FIG. 1 and used in an area from the ascending aorta to the aortic arch. The bare stent is made of a nickel-titanium material, and is formed by interleaving 120 first wires with a diameter of 100 μm and 8 second wires with a diameter of 400 μm. The bare stent is woven into four layers in a return weaving manner. The return weaving manner is shown in C in FIG. 5. In this figure, the proximal end is a smooth tip which is woven in a return weaving manner completely. At the distal end, two layers of burrs are located at the inner side of the stent, and two layers of edges, which are woven in a return weaving manner, are located at the outer side of the stent, thereby preventing the burrs from being exposed to damage the vessel wall.

A portion of the bare stent corresponding to the ascending aorta has a diameter of 45 mm and a length of 9 cm, and a portion of the bare stent corresponding to the aortic arch has a diameter of 32 mm and a length of 6 cm. A sparse mesh area is provided at 30 mm from the proximal end of the bare stent, and the sparse mesh area has a length of 6 cm and an arc length of ⅓ the circumference.

As detected by a scanning electron microscope, a metal coverage of the stent in this embodiment in a natural state is 80% except for the sparse mesh area, and a metal coverage of the stent after axial maximum compression is about 98%. As detected by a radial support force tester, a radial support force of a thicker portion of the stent in this embodiment corresponding to the ascending aorta in the natural state is about 400 N, a radial support force of a portion provided with the sparse mesh area is about 100 N, and a radial support force after the axial maximum compression is greater than 400 N, even up to 500 N or more.

In addition, in order to simulate a situation of axial bending stress of the stent when the stent is fixed at the aortic arch, a radial straightening force of the stent is measured between 0.4 N and 1.0 N.

The forgoing is only part of specific embodiments of the disclosure, and thus is not intended to limit the patent scope of the disclosure. Any equivalent structural transformation made by using the description and accompanying drawings of the disclosure within the inventive concept of the disclosure, or directly/indirectly applied to other related technical fields, is included within the patent scope of protection of the disclosure.

What is claimed is:
1. An axially compressible and stretchable bare stent, used in an aorta, the bare stent comprising:
   a non-sparse mesh area, wherein the non-sparse mesh area is formed by overlapping and interleaving at least first wires and second wires, each of the first wires and each of the second wires having different diameters, wherein a diameter of each of the first wires ranges from 20 μm to 150 μm, and a diameter of each of the second wires ranges from 150 μm to 600 μm; and
   a first sparse mesh area and a second sparse mesh area, wherein each of the first sparse mesh area and the second sparse mesh area is formed only of the second wires, and each of the first sparse mesh area and the second sparse mesh area is configured to be arranged at branch arteries of a corresponding treatment site after the bare stent is released,
   wherein the bare stent is provided with at least two layers of woven meshes;
   wherein in a natural release state, except for the first sparse mesh area and the second sparse mesh area, the bare stent has a metal coverage of at least 60%;
   wherein the second wires comprise first thick wires and second thick wires, each of the first thick wires and each of the second thick wires having different diameters, wherein a diameter of each of the first thick wires ranges from 150 μm to 300 μm, and a diameter of each of the second thick wires ranges from 300 μm to 600 μm;
   wherein the bare stent is formed by weaving 96-202 wires, among which the second wires comprise 6-12 first thick wires and 4-12 second thick wires, and remaining wires are the first wires.
2. The axially compressible and stretchable bare stent according to claim 1, wherein in the natural release state, a radial support force of the bare stent is greater than or equal to 100 N.
3. The axially compressible and stretchable bare stent according to claim 2, wherein in the natural release state, the radial support force of the bare stent ranges from 100 N to 600 N; and except for the first sparse mesh area and the second sparse mesh area, the bare stent has the metal coverage of 70%-90%.
4. The axially compressible and stretchable bare stent according to claim 2, wherein except for the first sparse mesh area and the second sparse mesh area, the bare stent is formed by weaving the first wires and the second wires in a uniformly distributed manner.
5. The axially compressible and stretchable bare stent according to claim 1, wherein when the bare stent is placed in the aorta, the bare stent has different degrees of compression in a length direction of the bare stent.
6. The axially compressible and stretchable bare stent according to claim 1, wherein in a release and axial maximum compression state, the bare stent has the metal coverage of 90%-100%.
7. The axially compressible and stretchable bare stent according to claim 1, wherein in a release and axial maximum compression state, a radial support force of the bare stent is greater than or equal to 500 N.
8. The axially compressible and stretchable bare stent according to claim 7, wherein in the release and axial maximum compression state of the bare stent, the radial support force of the bare stent ranges from 500 N to 1000 N.
9. The axially compressible and stretchable bare stent according to claim 1, wherein the bare stent is used in an area from an ascending aorta to an abdominal aorta, the area comprising at least the ascending aorta, and the first sparse mesh area being configured to be arranged at an aortic arch site.
10. The axially compressible and stretchable bare stent according to claim 1, wherein the bare stent is used in an area from an ascending aorta to an abdominal aorta, the area comprising at least the abdominal aorta, the second sparse mesh area being configured to be arranged at branch artery sites in the abdominal aorta, wherein the branch arteries in the abdominal aorta are a left renal artery, a right renal artery, a coeliac trunk and a superior mesenteric artery, which are located on the abdominal aorta.

11. The axially compressible and stretchable bare stent according to claim 1, wherein the bare stent is internally provided with two common iliac artery stent fixing parts.

12. The axially compressible and stretchable bare stent according to claim 11, wherein the two common iliac artery stent fixing parts are arranged inside the bare stent and correspond to the abdominal aorta close to a bifurcation of left and right common iliac arteries, and the two common iliac artery stent fixing parts are configured as two annuluses tangent to each other and are integrally formed with an inner wall of the bare stent.

13. The axially compressible and stretchable bare stent according to claim 1, wherein the bare stent has a variable diameter, wherein the diameter of the bare stent ranges from 20 mm to 60 mm.

14. The axially compressible and stretchable bare stent according to claim 13, wherein a diameter of a portion of the bare stent ranges from 38 mm to 60 mm.

15. The axially compressible and stretchable bare stent according to claim 1, wherein the first wires comprise first thin wires and second thin wires, each of the first thin wires and each of the second thin wires having different diameters, wherein a diameter of each of the first thin wires ranges from 50 μm to 100 μm, and a diameter of each of the second thin wires ranges from 100 μm to 150 μm.

16. An axially compressible and stretchable bare stent, used in an aorta, the bare stent comprising:

a non-sparse mesh area, wherein the non-sparse mesh area is formed by overlapping and interleaving at least first wires and second wires, each of the first wires and each of the second wires having different diameters, wherein a diameter of each of the first wires ranges from 20 μm to 150 μm, and a diameter of each of the second wires ranges from 150 μm to 600 μm; and a first sparse mesh area and a second sparse mesh area, wherein each of the first sparse mesh area and the second sparse mesh area is formed only of the second wires, and each of the first sparse mesh area and the second sparse mesh area is configured to be arranged at branch arteries of a corresponding treatment site after the bare stent is released, wherein the bare stent is provided with at least two layers of woven meshes;

wherein in a natural release state, except for the first sparse mesh area and the second sparse mesh area, the bare stent has a metal coverage of at least 60%;

wherein the first wires comprise first thin wires and second thin wires, each of the first thin wires and each of the second thin wires having different diameters, wherein a diameter of each of the first thin wires ranges from 50 μm to 100 μm, and a diameter of each of the second thin wires ranges from 100 μm to 150 μm;

wherein the bare stent is formed by weaving 96-202 wires, among which 4-30 wires are the second wires, and remaining wires are the first wires, wherein the first wires comprises 32-166 first thin wires and 32-166 second thin wires, provided that a sum of a number of the first thin wires and a number of the second thin wires is less than or equal to 198.

* * * * *